US005598316A

United States Patent [19]
Kasting, Jr.

[11] Patent Number: 5,598,316
[45] Date of Patent: *Jan. 28, 1997

[54] METHOD FOR REDUCING STATIC ELECTRICAL CHARGES BY APPLICATION OF OZONATED WATER

[75] Inventor: John R. Kasting, Jr., Waxhaw, N.C.

[73] Assignee: OxiDyn, Incorporated, Monroe, N.C.

[*] Notice: The term of this patent shall not extend beyond the expiration date of Pat. No. 5,368,815.

[21] Appl. No.: 327,312

[22] Filed: Oct. 21, 1994

Related U.S. Application Data

[63] Continuation-in-part of Ser. No. 986,055, Dec. 7, 1992, Pat. No. 5,368,815.

[51] Int. Cl.$^6$ ............................................. H05F 1/00
[52] U.S. Cl. .......................... 361/212; 361/228; 422/3; 422/186.12; 422/186.14
[58] Field of Search .................... 422/3, 24, 28, 422/29, 31, 186.07, 186.14, 302, 186.08–186.13, 186.15–186.2, 907; 361/212, 213, 215, 225, 227, 228; 8/474

[56] References Cited

U.S. PATENT DOCUMENTS

| | | | |
|---|---|---|---|
| 1,157,908 | 10/1915 | Steynis | 8/374 |
| 2,569,116 | 9/1951 | Roscoe et al. | 422/186.12 |
| 3,029,121 | 4/1962 | Collins | 8/374 |
| 3,958,066 | 5/1976 | Imamura et al. | 361/212 |
| 4,409,188 | 10/1983 | Silberzahn | 422/28 |
| 4,680,163 | 7/1987 | Blidschun et al. | 422/28 |
| 5,356,592 | 10/1994 | Balla et al. | 422/28 |
| 5,368,815 | 11/1994 | Kasting et al. | 422/3 |

FOREIGN PATENT DOCUMENTS

| | | | |
|---|---|---|---|
| 3440315 | 5/1986 | Germany | 422/186.07 |
| 636829 | 12/1978 | U.S.S.R. | 361/215 |
| 1195487 | 11/1985 | U.S.S.R. | 422/186.07 |

Primary Examiner—Joseph W. Drodge
Attorney, Agent, or Firm—Bell, Seltzer, Park & Gibson, P.A.

[57] ABSTRACT

An apparatus and method for substantially eliminating static electrical charges from articles by rinsing the articles with ozonated water is disclosed. A closed loop recirculating system for ozonated water is described. The apparatus provides a pressure differential bypass line for providing a constant recirculating flow of ozonated water from an venturi for injecting ozone into the water directly to a water storage tank, by-passing a rinsing apparatus. Also included are a supply line to a rinsing apparatus and a diverted supply line for diverting flow back to the storage tank and bypassing the rinser apparatus. The supply line and the diverted supply line have a normally closed solenoid valve and a normally open solenoid valve, respectively, for controlling the flow of ozonated water between them. A pair of redox probes are provided for monitoring ozone concentration in the water and determining whether to initiate or to cease rinser operation. In this manner, the apparatus and process provides for automatic detection of contaminants and a shutdown of rinser operation and maintains and regulates pressure and volume of water for optimizing injection of ozone into the water and for maintaining ozone in the water.

12 Claims, 3 Drawing Sheets

5,598,316

METHOD FOR REDUCING STATIC ELECTRICAL CHARGES BY APPLICATION OF OZONATED WATER

This application is a continuation-in-part of U.S. Ser. No. 07/986,055, which was filed on Dec. 7, 1992, now U.S. Pat. No. 5,368,815 and is entitled "Process and Apparatus for Sanitizing Articles."

FIELD OF THE INVENTION

This invention relates to a method for ozonating water and supplying water containing ozone for contacting with articles.

BACKGROUND OF THE INVENTION

Manufacturers of food products and beverages for human consumption typically package the beverage or food product. A variety of substances may be used to provide packaging for the products, including, but not limited to, plastics, aluminum, and glass. As a specific example, soft drinks and other beverages typically are packaged in bottles formed from polyethylene terephthalate, otherwise known as "PET bottles." However, other plastics are also well known to the beverage and food packaging industries for use as containers for food and beverage products.

Current practice in the industry, and in particular for the packaging of soft drinks, is to rinse PET bottles and aluminum beverage cans with municipal water prior to filling the bottle with a soft drink. The use of hot water or chemical disinfectants typically has not been considered suitable for rinsing PET bottles and aluminum beverage cans prior to filling because hot water or disinfectants could chemically or physically alter the characteristics of a PET bottle or an aluminum beverage can liner. Such alterations could render the bottles or cans unsuitable for containing beverages, or adversely affect the quality or taste of the beverage, or render the beverage unsuitable for human consumption.

Various devices and processes have been proposed for sanitizing containers such as bottles and cans by contact with an ozonated rinse water. Ozone is highly reactive and is an effective oxidizing agent for sanitizing containers. Ozonated rinse water has the advantage over untreated rinse water of effectively removing microbes and other contaminants without changing the chemical or physical nature of the container. For example, Silberzahn U.S. Pat. No. 4,409,188 proposes a device for sterilizing containers that comprises a rotatable immersion wheel for immersing the containers in a bath of ozone and water. Numerous other devices using ozone as a sanitizing agent have also been proposed.

Hughes U.S. Pat. No. 5,106,495 proposes a portable water purification device that uses ozone as a treatment agent. Water in a tank is circulated by a pump through a venturi where ozone is injected into the water, which is then returned to the tank.

Burris U.S. Pat. No. 5,082,558 proposes a contact lens purification system in which sensors detect the concentration of ozone in the treatment liquid, and a controller acts responsibly to the sensor to control the residence time of the lenses in the system in response to the concentration of ozone.

McConnell et al. U.S. Pat. No. 4,795,497 proposes a method and a system for the fluid treatment of semiconductor wafers in a sequence of fluids and uses a closed fluid recirculation loop and a means for holding the wafers in the fluid flow path. In one embodiment, ozone is bubbled through the treatment fluid to enhance cleaning.

In spite of these previous devices and methods for using ozone as a sterilizing or cleaning agent, the food and beverage industry, and in particular the soft drink industry, still relies on municipal water supplies for rinsing PET containers and aluminum cans prior to filling with soft drink or other beverages such as fruit juice based beverages and sport drinks. The rinse water typically is not recirculated, resulting in the run off of thousands of gallons of waste water and the high costs of operation associated with such a great use of municipal water supplies.

The PET bottles stick together due to static electrical charges and operator personnel sometimes apply additional quantities of food grade lubricants to the bottle handling equipment to compensate. The lubricants stick to the bottles and often are not substantially removed prior to filling with beverage. Increased use of these lubricants can lead to undesirable increased biological and chemical oxygen demand in waste water and causes problems in the plant sewer discharge and increases the cost of sewer discharge.

Copending patent application U.S. Ser. No. 07/986,055, which was filed on Dec. 7, 1992, now U.S. Pat. No. 5,368,815 and is entitled "Process and Apparatus for Sanitizing Articles," describes an apparatus and process for using ozonated water for sanitizing various articles, including PET bottles for the soft drink industry. Subsequently, it was recognized that more debris appeared to be removed from PET bottles and other articles such as aluminum beverage cans with ozonated rinse water than was previously removed with municipal water supplies and that the problem of food containers sticking together was reduced. Static electrical charges associated with the food containers were substantially eliminated by application of ozonated water.

SUMMARY OF THE INVENTION

The invention relates to a method for using ozonated water to substantially reduce or eliminate static electrical charges on various articles. Substantially reducing the static electrical charge on articles such as PET bottles and aluminum beverage cans reduces the amount of debris and other substances that sometimes adhere to the interior and exterior surfaces of the articles and typically are not removed by rinsing with municipal water supplies. Reducing static electrical charges also reduces the likelihood of attraction to the article of air borne contaminants such as molds and bacteria that potentially could contaminate a beverage or other food grade product. By rinsing the articles with ozonated rinse water using the method of the invention, a substantially cleaner food or beverage container or other article can be obtained.

The method comprises supplying water from a source for ozonation, injecting ozone into the water, contacting articles having a static electrical charge with the ozonated water, and substantially reducing the static electrical charge.

In a more specific embodiment, the method is characterized by automatic recirculating flow of a captive water supply. The method comprises supplying water from a source for ozonation, injecting ozone into the water, and returning at least a predetermined first portion of the ozonated water to the source. A predetermined second portion of the ozonated water is alternately supplied for substantially eliminating static electrical charges on articles or is returned to the source, bypassing the articles. When the predetermined second portion of ozonated water is supplied for substantially eliminating static electrical charges on articles, then the used ozonated water is also returned to the storage vessel.

In a more specific embodiment, the method includes the steps of establishing a set point for a minimum concentration of ozone in the water, monitoring the concentration of ozone in the water prior to supplying ozonated water to the articles for rinsing, and supplying ozonated water to the articles when the monitored concentration of the ozone in the water is above the minimum.

In another specific embodiment, the method comprises the steps of establishing a set point for a maximum loss of ozone concentration over time, monitoring the concentration of ozone in the water with respect to time after supplying ozonated water to articles for rinsing, and ceasing to supply ozonated water to the articles when the monitored concentration of ozone exceeds the set point for a maximum loss over time. In this manner, if a contaminant, such as a hydrocarbon contaminant, causes the ozone level to drop very quickly, then the rinsing method can be halted until the condition is corrected. However, minor or slow fluctuations in the ozone level need not interrupt the method.

DETAILED DESCRIPTION OF THE PREFERRED EMBODIMENTS

Figure 1:
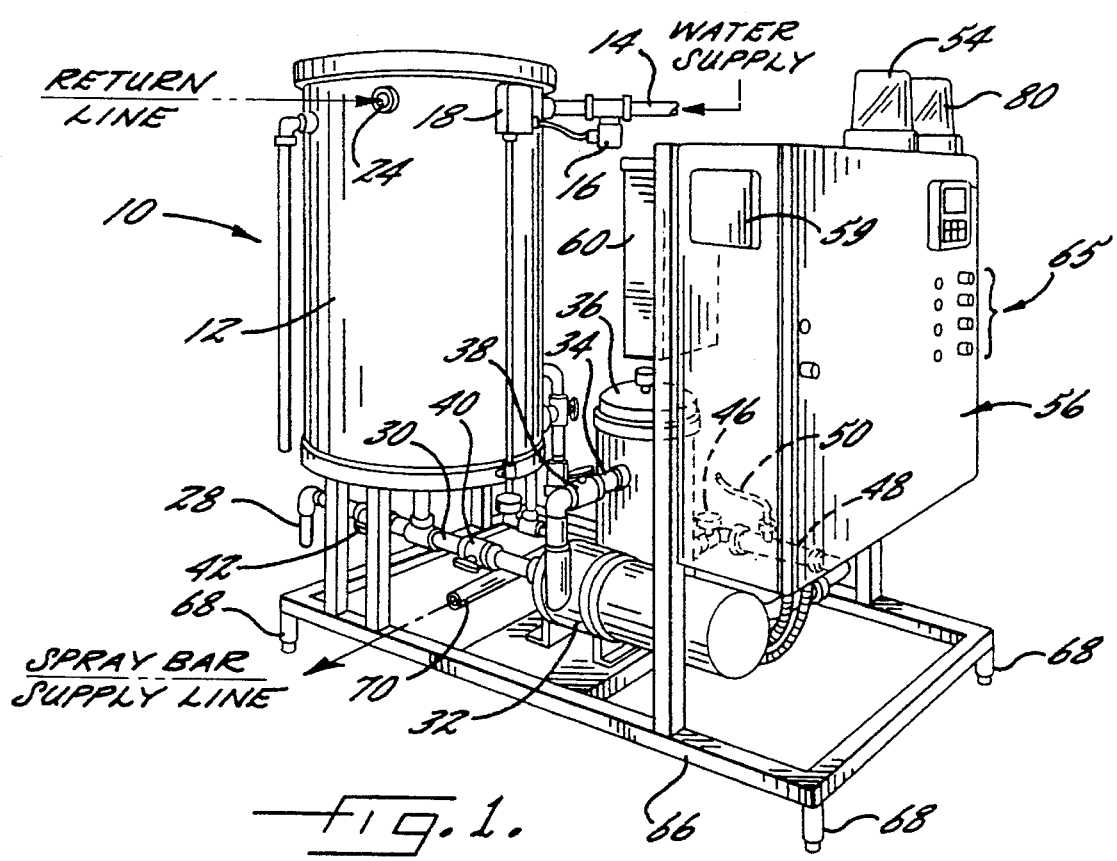
FIG. 1 is a perspective view of a preferred embodiment of an apparatus for use in practicing the method of the invention.

FIG. 1 shows broadly at 10 a perspective view of a preferred embodiment of the apparatus of the invention. The apparatus includes a storage vessel for supplying ozonated water, storage tank 12, in which an ozonated water supply is stored and maintained. The storage tank and other components of the apparatus that come into contact with ozonated water should be constructed of materials that are resistant to oxidation, such as polyethylene, polyvinylchloride, or, most preferred for rigid bodies, stainless steel. However, additional plastics and some other materials will also be suitable for use in practice of the present invention, as will be recognized by the skilled artisan.

Figure 2:
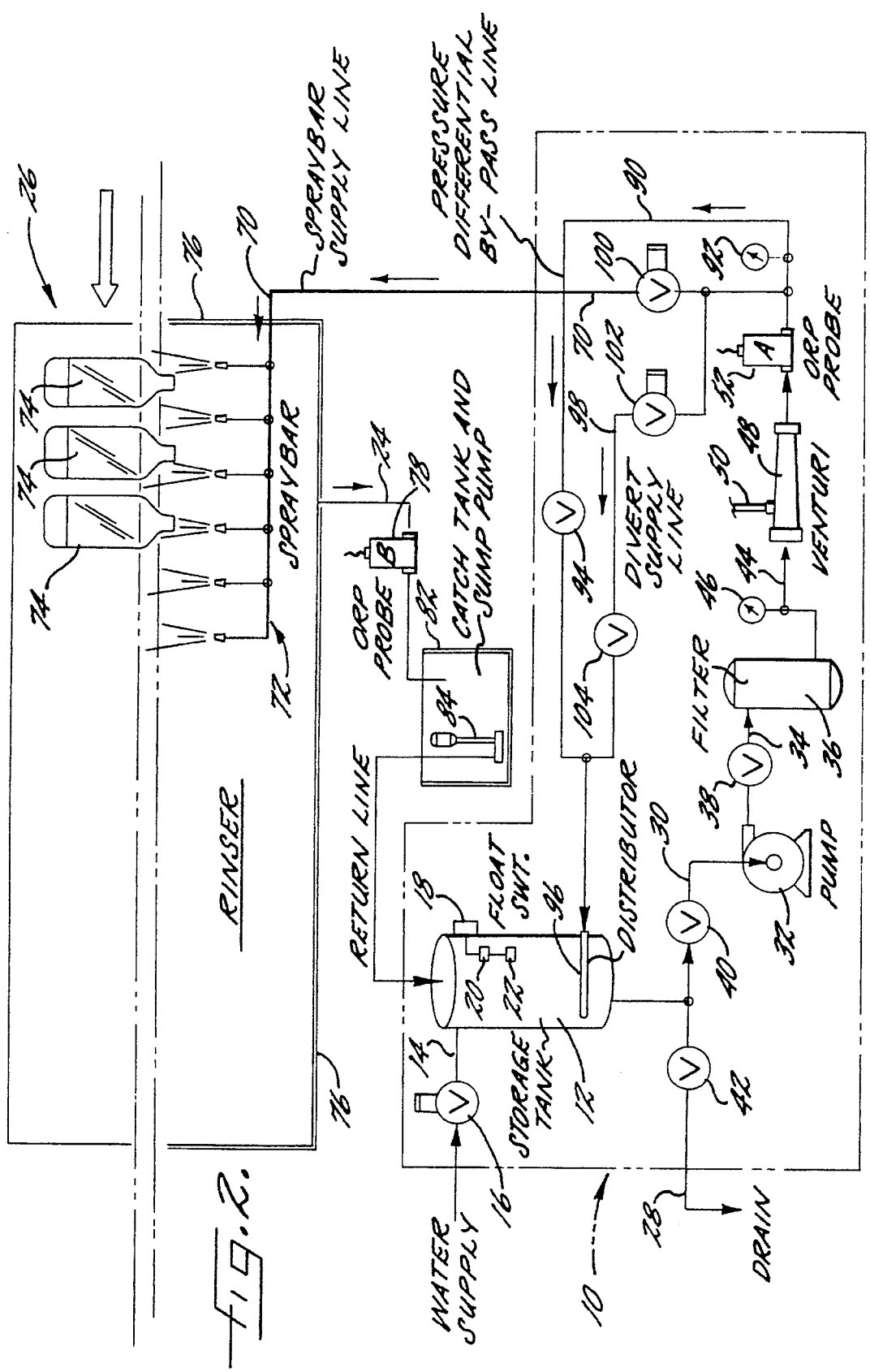
FIG. 2 is a highly schematic flow diagram showing interconnection of the apparatus of FIG. 1 with a device for contacting PET soft drink bottles with ozonated rinse water.

Storage tank 12 includes a water supply 14 by which the storage tank is filled with water initially and through which make up water can be added as needed. A suitable electrical control, solenoid valve 16, is provided on the water supply conduit for automatic on/off operation of the water supply line. The solenoid valve is connected to a float switch 18 (FIG. 2). Float switch 18 monitors the level of water in the tank 12 and indicates when the tank 12 is full and when water should be added to the tank to maintain a minimum level. Preferably, the float switch is a stainless steel dual float assembly providing for high and low water levels 20 and 22 respectively. Additionally, a secondary timing device is preferably included to automatically displace any excess heat built up in the storage tank.

A return line 24 is also provided on the storage tank for return of ozonated rinse water from a PET bottle rinser 26 (FIG. 2). Also shown in FIG. 1, is a drain line 28 from the storage tank through which the tank may be emptied of water. Rinse water is supplied from the storage tank for injection of ozone through conduit 30.

Water in conduit 30 is supplied from the storage tank to a pump 32. Pump 31 provides a means for circulating fluid throughout the system. The pump components for contact with ozonated water should be made of a material resistant to oxidation, preferably stainless steel. The skilled artisan will recognize that the pump should be selected and sized based on the volume of fluid to be transported through the system. Water exits the pump through a conduit 34 and enters a particulate filter 36 for removal of solid contaminants that may enter the fluid circulating lines through the rinsing process. The particulate filter housing and filtration components should be constructed of materials resistant to oxidation by ozone, as will be recognized by the skilled artisan.

A valve 38 is included on fluid flow line 34 by which flow to filter 36 may be regulated. Valve 38 is a ball valve and will be used primarily for isolating components of the system, such as the filter, should it become necessary to change the filter elements. The skilled artisan will recognize that other types of valves may be selected. A similar valve 40 is included on conduit 30 from the storage tank to the pump. Together, valves 40 and 38 provide a convenient method for isolating the pump should it become necessary to perform maintenance procedures on the pump or to remove the pump from the system. Also, a similar valve 42 is included on conduit 28 for controlling flow of fluid from the storage tank through the drain line 28.

After exiting filter 36, the fluid enters a conduit 44 shown in FIG. 1 in shadow behind additional components to be discussed hereinbelow. A pressure gauge 46 is shown on line 44 just prior to ozone injecting means, venturi 48. Ozone containing gas is supplied to venturi 48 through a gas line 50 for injection into the water as it passes through the venturi. A venturi provides a short section of a gradually tapering, more constricted flow path for the fluid in the pipe that results in an increase in the velocity of the fluid and a corresponding reduction in fluid pressure. Together, fluid flow conduits 30, 34, and 44 form a first fluid flow conduit interconnecting the storage tank 12 and the venturi 48. The skilled artisan will recognize that the venturi should be made from materials suitable for use in a system for supplying rinse water to packaging for food grade products.

Figure 3:
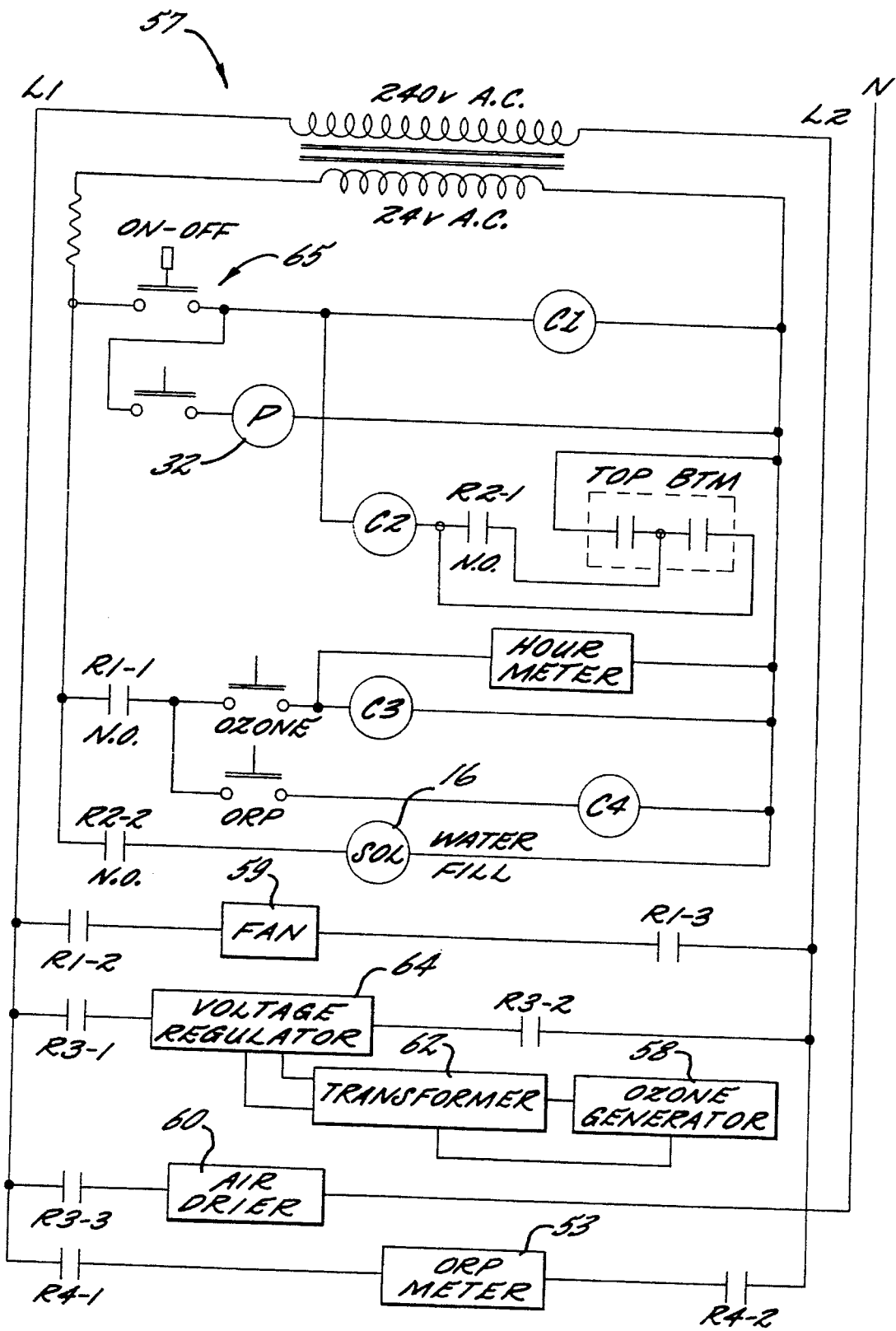
FIG. 3 is a simplified and highly schematic diagram of the electrical components of the apparatus as illustrated in FIG. 1.

Ozonated water is then conveyed from the venturi through an ORP probe (redox, or Oxidation Reduction Probe) 52 (FIG. 2) which is inserted into an access port in the conduit and monitors the level of ozone in the rinse water. The ORP probe 52 provides an output relay to an ORP meter 53 (FIG. 3) depending on a set point for a low level of ozone concentration. The output relay can be used to initiate a warning light 54 (FIG. 1) or can be connected directly to the rinser to shut down operation of the rinser in the event of a low ozone concentration.

The ozone generating system for supplying ozone containing gas to the venturi 48 for injection into the water is contained within housing 56 illustrated in FIG. 1. The components of the ozone generating system are illustrated schematically in the simplified electrical diagram of FIG. 3 at 57. An ozone generator 58 generates ozone from dry compressed air and supplies ozone containing air to venturi 48. Preferably, ozone generator 58 should comprise a mercury free corona lamp spaced from a stainless steel chamber having internal and external flow passages for dry air for ozone generation and to provide adequate cooling capacity for the chambers of the ozone generator. A corona lamp for an ozone generator of this description is available from LCD Lighting, Inc., 11 Cascade Boulevard, Milford, Conn. 06460-0870. Multiple corona tubes with stainless steel jackets can be incorporated in parallel into a single generator for greater ozone producing capacity. A fan 59 is used to supply air to the interior of housing 56 to provide cooling for the equipment.

Air to be supplied to the ozone generator should be dry. A suitable air dryer 60 (FIGS. 1 and 3) for use in connection with the practice of the invention claimed herein is available from Domnick Hunter, Inc., having worldwide offices and an office at 6636-D East W. T. Harris Boulevard, Charlotte, N.C. 28215. Specifically, Domnick Hunter sells a self-regenerating air dryer having a −100° degree Fahrenheit dew point. The desiccant is a nitrogen-reducing mixed bed type. The air dryer includes filters prior to and after the desiccant with 0.01 micron filter elements and a water separator. This air dryer is self-regenerating and has a timer circuitry. Air is supplied to the air drier using any suitable compression means, as will be known to the skilled artisan.

Power is supplied to the ozone generator by a transformer 62. Power is supplied to the air dryer and other components as line voltage. It is preferable in the practice of the invention claimed herein to use an inductive, step-up high voltage transformer. The transformer should have a primary or input voltage compatible with the power source. Typically, this high voltage transformer will have a 240 VAC 50/60 cycle primary and a 9,000 volt secondary for operating corona lamps in parallel; although other values may be selected depending on need. Secondary voltage can vary from about 8,000 to 12,000 volts. A suitable transformer is available from Magnetics and Controls, Inc., Rosemont, N.J. 08556.

A voltage regulator 64 should be used to provide a stable and consistent voltage for the ozone generator and the ORP meters. Power is supplied to the various components by a series of on/off switches 65 on housing 56.

As illustrated FIG. 1, the entire apparatus 10 is a portable unit and is mounted on a stand 66 having adjustable legs 68. The entire unit can be conveniently moved for attachment to an apparatus for supplying ozonated water for contact with articles for rinsing and for return of water to the storage tank 12 Although a PET bottle rinsing apparatus such as that used in the soft drink industry is illustrated, the skilled artisan will recognize that the apparatus of FIG. 1 could be interconnected with any number of apparatus for supplying ozonated rinse water for rinsing articles. For example, the apparatus of FIG. 10 could be connected for supplying ozonated water to and receiving the used water from a depalletizer for removing bottles and cans from shipping containers prior to filling.

The skilled artisan should recognize that the supply line 71 can be placed in fluid flow communication with more than one apparatus for contacting articles with ozonated water. The length of the line over which the ozonated water can travel and retain its ozone concentration typically will not exceed about 100 linear feet or its equivalent. The return line 24 likewise can receive flow from more than one contacting apparatus so that the water can be returned to the storage tank 12. Various valves and fittings can be used to control the flow rate of the ozonated water to and from each contacting apparatus to which the apparatus 1 is connected and such is believed to be apparent to the skilled artisan.

FIG. 2 illustrates a highly schematic flow diagram of the apparatus 10 of FIG. 1 interconnected with a spray bar supply line 70 for supplying ozonated water to a spray bar 72 for spraying PET soft drink bottles 74. Spray bar 72 is located in a rinser shown broadly at 26. PET bottles are advanced in the direction of the arrow through the rinser where the PET bottles are contacted with a spray of ozonated water from the spray bar 72. Rinser 26 provides a collecting pan 76 by which the rinse water is collected after being sprayed on the bottles. A return line 24 conveys the used rinse water from the collecting pan to the storage tank 12. A second ORP probe (redox or Oxidation Reduction Probe) 78 is included in an access port in return line 24. As will be recognized by the skilled artisan, a single ORP probe can be used to access both the ports at each location shown in FIG. 2 as ORP probe 52 and ORP probe 78. If more than one ORP probe is used, then it shall be necessary to use two ORP meters. ORP probe 78 provides a relay to an ORP meter such as at 53 (FIG. 3) in the event that ozone concentration drops below a predetermined level within a predetermined short period of time. For example, ozone typically is supplied for contact with articles through the apparatus and process of the invention at a concentration of from about 0.2 to 0.6 or more mg/l of ozone in aqueous solution to ensure removal of static electrical charge. This level of ozone concentration is typically also sufficient for sterilization. The meter can be set to respond if the ORP probe shows a 20 mV drop in 3 seconds. If the ozone level drops too fast, then a contaminant situation is indicated, such as a hydrocarbon, that could necessitate stopping the rinser, either by stopping conveyance of the bottles through the rinser or by stopping the flow of ozonated water. The ORP probe 78 can provide a relay to initiate a warning signal via a lamp 80 (FIG. 1) or to stop the rinser operation. ORP probe 78 thereby provides an in-line contaminant detection sensing capability.

A catch tank 82 and sump pump 84 are also included in return line 24 for providing flow of collected and used rinse water to the storage tank 12. Together, fluid flow conduits 30, 34, 44, which constitute a first fluid flow conduit from the storage tank to the venturi; second fluid flow conduit 70; and third fluid flow conduit 24 provide a closed loop recirculating system for conveyance and return of a captive ozonated water supply.

In addition to the storage tank 12, the pump 32, the filter 36, the venturi 48, and associated flow lines discussed in connection with FIG. 1, FIG. 2 also illustrates a means for providing bypass recirculation of ozonated water from the venturi directly to the storage tank. Pressure differential bypass line 90 constitutes a forth fluid flow conduit that along with associated pressure gauge 92 and metering valve 94 provide a constant recirculating flow of ozonated water from the venturi 48 to the storage tank 12. A distributor 96 is included in storage tank 12 for distributing the ozonated water via line 90 into the storage tank. Distributor 96 is preferably a manifold type with numerous orifices provided for bubbling the ozone containing water into the water contained in the storage tank. In this manner, a constant supply of freshly ozonated water is supplied to the water in the storage tank.

Additionally, a fifth fluid flow conduit, line 98 is provided for diverting the supply of ozonated water from spray bar supply line 70 back to the storage tank 12, bypassing spray bar 72. As illustrated, the diverted supply line 98 joins line 90 and enters distributor 96 for distributing freshly ozonated water into storage tank 12. As will be recognized by the skilled artisan, supply line 98 could be supplied as a separate line to storage tank 12.

Spray bar supply line 70 and diverted supply line 98 each include solenoid valves 100 and 102, respectively, for controlling the flow of ozonated water. Solenoid valve 100 is a normally closed solenoid that is open to supply ozonated water to the spray bar 72. Solenoid valve 102 in the diverted supply line is a normally open solenoid for diverting supply of ozonated water from supply line 71 to storage tank 12 via line 98. In this manner, a predetermined flow of ozonated water is recirculated through the system from the venturi 48 through the diverted supply line 98 to the storage tank 12 when solenoid 12 is in its normally opened position.

When operation of the rinser 26 is commenced, then normally opened solenoid 102 closes and normally closed solenoid 100 opens to supply a predetermined flow of ozonated water to the spray bar 72 for collection in collecting pan 76 and return via return line 24 to the storage tank 12. As can be seen, recirculating flow to the storage tank is maintained between a first limit, which corresponds to flow through line 90, and a second limit, which corresponds to the combined flows through line 90 and diverted supply line 98. Metering valves 94 in line 90 and 104 in line 98 are provided to throttle and regulate pressure and back pressure to optimize injection of ozone into the water at the venturi and to maintain ozone in the water as it is sprayed through the spray bar 72 onto bottles 74.

The following tables show values in millivolts of static electrical charges on bottles and cans at several points along the processing line of a typical beverage bottling plant, before and after rinsing with ozonated water in accordance with the invention (Tables 1 and 2) and rinsing with municipal water (Tables 3 and 4). Use of ozonated rinse water in accordance with the invention is seen clearly to reduce or eliminate altogether static electrical charges as compared to rinsing with municipal rinse water.

TABLE 1

| Bottle Containers | Palletizer Before Rinser | After Rinser | Prior To Filler | After Capper | After Packaging Shrink Wrap |
|---|---|---|---|---|---|
| 1 | −500 | 0 | 0 | 0 | 0 |
| 2 | −500 | 0 | 0 | 0 | 0 |
| 3 | −375 | 0 | 0 | 0 | 0 |
| 4 | −125 | 0 | 0 | 0 | 0 |
| 5 | −500 | 0 | 0 | 0 | 0 |
| 6 | −500 | 0 | 0 | 0 | 0 |
| 7 | −500 | 0 | 0 | 0 | 0 |
| 8 | −500 | 0 | 0 | 0 | 0 |
| 9 | −450 | 0 | 0 | 0 | 0 |
| 10 | −350 | 0 | 0 | 0 | 0 |
| 11 | −476 | 0 | 0 | 0 | 0 |
| 12 | −500 | 0 | 0 | 0 | 0 |
| 13 | −500 | 0 | 0 | 0 | 0 |
| 14 | −500 | 0 | 0 | 0 | 0 |
| 15 | −500 | 0 | 0 | 0 | 0 |
| 16 | −475 | 0 | 0 | 0 | 0 |
| 17 | −450 | 0 | 0 | 0 | 0 |
| 18 | −500 | 0 | 0 | 0 | 0 |
| 19 | −500 | 0 | 0 | 0 | 0 |
| 20 | −500 | 0 | 0 | 0 | 0 |
| 21 | −500 | 0 | 0 | 0 | 0 |
| 22 | −500 | 0 | 0 | 0 | 0 |
| 23 | −500 | 0 | 0 | 0 | 0 |
| 24 | −500 | 0 | 0 | 0 | 0 |
| 25 | −500 | 0 | 0 | 0 | 0 |

TABLE 2

| Can Containers | Palletizer Before Rinser | After Rinser | Prior To Filler | After Filler | After Shrink Wrap |
|---|---|---|---|---|---|
| 1 | −500 | 0 | 0 | 0 | 0 |
| 2 | −500 | 0 | 0 | 0 | 0 |
| 3 | −500 | 0 | 0 | 0 | 0 |
| 4 | −500 | 0 | 0 | 0 | 0 |
| 5 | −500 | 0 | 0 | 0 | 0 |
| 6 | −500 | 0 | 0 | 0 | 0 |
| 7 | −500 | 0 | 0 | 0 | 0 |
| 8 | −500 | 0 | 0 | 0 | 0 |
| 9 | −500 | 0 | 0 | 0 | 0 |
| 10 | −500 | 0 | 0 | 0 | 0 |
| 11 | −500 | 0 | 0 | 0 | 0 |
| 12 | −500 | 0 | 0 | 0 | 0 |
| 13 | −500 | 0 | 0 | 0 | 0 |
| 14 | −500 | 0 | 0 | 0 | 0 |
| 15 | −500 | 0 | 0 | 0 | 0 |
| 16 | −500 | 0 | 0 | 0 | 0 |
| 17 | −500 | 0 | 0 | 0 | 0 |
| 18 | −500 | 0 | 0 | 0 | 0 |
| 19 | −500 | 0 | 0 | 0 | 0 |
| 20 | −500 | 0 | 0 | 0 | 0 |
| 21 | −500 | 0 | 0 | 0 | 0 |
| 22 | −500 | 0 | 0 | 0 | 0 |
| 23 | −500 | 0 | 0 | 0 | 0 |
| 24 | −500 | 0 | 0 | 0 | 0 |

TABLE 3

| PET Bottles | Before Rinser | After City Water Rinser | Prior To Filler | After Capper | After Shrink Wrap |
|---|---|---|---|---|---|
| 1 | −500 | −100 | −100 | 0 | −500 |
| 2 | −500 | −100 | −100 | 0 | −500 |
| 3 | −500 | −100 | −100 | 0 | −500 |
| 4 | −500 | −100 | −100 | 0 | −500 |
| 5 | −500 | −100 | −100 | 0 | −500 |
| 6 | −500 | −100 | −100 | 0 | −500 |
| 7 | −500 | −100 | −100 | 0 | −500 |
| 8 | −450 | −100 | −100 | 0 | −500 |
| 9 | −500 | −100 | −100 | 0 | −500 |
| 10 | −250 | −50 | −100 | 0 | −500 |
| 11 | −300 | 0 | −50 | 0 | −500 |
| 12 | −500 | −100 | −100 | 0 | −500 |
| 13 | −150 | −50 | −100 | 0 | −500 |
| 14 | −150 | 0 | −50 | 0 | −500 |
| 15 | −150 | 0 | −100 | 0 | −500 |
| 16 | −200 | −50 | −100 | 0 | −500 |
| 17 | −150 | −150 | −100 | 0 | −500 |
| 18 | −225 | −100 | −100 | 0 | −500 |
| 19 | −200 | −150 | −50 | 0 | −500 |
| 20 | −100 | −100 | −100 | 0 | −500 |
| 21 | −100 | −100 | −200 | 0 | −500 |
| 22 | −150 | −150 | −200 | 0 | −500 |
| 23 | −200 | −100 | −100 | 0 | −500 |
| 24 | −250 | −50 | −100 | 0 | −500 |
| 25 | −350 | −100 | −100 | 0 | −500 |

TABLE 4

| Can Containers | Before Rinse | After City Water Rinser | Prior To Filler | After Filler | After Shrink Wrap |
|---|---|---|---|---|---|
| 1 | −100 | −50 | −50 | 0 | −500 |
| 2 | −100 | −50 | −50 | 0 | −500 |
| 3 | −100 | −50 | −50 | 0 | −500 |
| 4 | −150 | −50 | −50 | 0 | −500 |
| 5 | −100 | 0 | 0 | 0 | −500 |
| 6 | −100 | −50 | −50 | 0 | −500 |
| 7 | −100 | −50 | −50 | 0 | −500 |
| 8 | −150 | −50 | −50 | 0 | −500 |
| 9 | −200 | −50 | −50 | 0 | −500 |
| 10 | −100 | 0 | 0 | 0 | −500 |
| 11 | −100 | 0 | 0 | 0 | −500 |
| 12 | −100 | −50 | −50 | 0 | −500 |

TABLE 4-continued

| Can Containers | Before Rinse | After City Water Rinser | Prior To Filler | After Filler | After Shrink Wrap |
|---|---|---|---|---|---|
| 13 | −100 | −50 | −50 | 0 | −500 |
| 14 | −100 | −50 | −50 | 0 | −500 |
| 15 | −100 | −50 | −50 | 0 | −500 |
| 16 | −100 | −50 | −50 | 0 | −500 |
| 17 | −50 | −50 | −50 | 0 | −500 |
| 18 | −100 | −100 | −100 | 0 | −500 |
| 19 | −100 | 0 | −50 | 0 | −500 |
| 20 | −100 | −100 | −100 | 0 | −500 |
| 21 | −100 | 0 | −50 | 0 | −500 |
| 22 | −100 | 0 | −50 | 0 | −500 |
| 23 | −100 | −50 | −50 | 0 | −500 |
| 24 | −100 | −100 | −50 | 0 | −500 |
| 25 | −100 | 0 | 0 | 0 | −500 |

The invention claimed herein has been described with respect to specific embodiments illustrated in the drawings. However, the skilled artisan will recognize that variations can be made within the scope and spirit of the invention as described in the foregoing specification and defined in the appended claims. While the invention has been described with reference to preferred embodiments, it should be understood that the invention is not intended to be limited to the embodiments illustrated in the drawings, to the rinsing of PET bottles and aluminum beverage cans for the beverage industry, or to other specific rinsing systems. On the contrary, the invention includes all alternatives, modifications, and equivalents that may be included within the scope and spirit of the invention as defined by the appended claims.

That which is claimed is:

1. A method for substantially eliminating static electrical charges from articles comprising the steps of:

(a) supplying water from a source thereof for ozonation;

(b) injecting ozone into the water for the ozonation;

(c) returning at least a predetermined first portion of the ozonated water to the source through means arranged for bypassing the articles;

(d) supplying a predetermined second portion of the ozonated water to the articles, when the concentration of ozone in the ozonated water is sufficient, for substantially eliminating static electrical charges associated with the articles; and (e) returning at least a substantial portion of the second portion of the ozonated water to the source.

2. A method according to claim 1 further comprising the steps of:

(a) establishing a set point for a minimum concentration of ozone in the water;

(b) monitoring the concentration of ozone in the ozonated water prior to supplying ozonated water; and (c) supplying ozonated water when the monitored concentration of the ozone in the water is above the minimum.

3. A method according to claim 2 wherein the step of supplying ozonated water is automatically controlled in response to the monitored concentration of ozone in the ozonated water.

4. A method according to claim 3 further comprising the step of sensing when articles are present for substantially eliminating static electrical charges and supplying ozonated water to the articles when said articles are present.

5. A method according to claim 1 further comprising the steps of:

(a) establishing a set point for maximum loss of ozone concentration over time;

(b) monitoring the concentration of ozone in the water being returned to the source with respect to time; and (c) ceasing to supply ozonated water when the monitored concentration of ozone in the water being returned to the source exceeds the set point for maximum ozone loss over time.

6. A method according to claim 5 wherein the step of ceasing to supply ozonated water is automatically controlled in response to the monitored concentration of ozone in the water being returned to the source.

7. A method for reducing static electrical charges on articles comprising the steps of:

(a) supplying water from a source thereof for ozonation;

(b) injecting ozone into the supplied water for ozonation;

(c) returning at least a predetermined first portion of the ozonated water to the source;

(d) establishing a set point for a minimum concentration of ozone in the ozonated water;

(e) monitoring the concentration of ozone in the water prior to supplying ozonated water to the articles for reducing static electrical charge;

(f) supplying a predetermined second portion of the ozonated water to the articles when the monitored concentration of the ozone in the water is above the minimum; and (g) returning the predetermined second portion of ozonated water to the source in combination with said first portion so that the second portion bypasses the articles when the monitored concentration of the ozone in the ozonated water is below the minimum.

8. A method for reducing static electrical charges on articles comprising the steps of:

(a) supplying water from a source thereof for ozonation;

(b) injecting ozone into the supplied water for ozonation;

(c) returning at least a predetermined first portion of the ozonated water to the source;

(d) supplying a predetermined second portion of the ozonated water to the articles to substantially eliminate static electrical charges from the articles;

(e) returning the second portion of ozonated water to the source;

(f) establishing a set point for maximum loss of ozone concentration over time;

(g) monitoring the concentration of ozone in the second portion of the water being returned to the source with respect to time;

(h) ceasing to supply ozonated water to the articles when the monitored concentration of ozone in the second portion of the water being returned to the source exceeds the set point for maximum ozone loss over time; and (i) returning the predetermined second portion of ozonated water to the source in combination with said first portion so that the second portion bypasses the articles when the supply of ozonated water to the articles is ceased.

9. A method for substantially eliminating static electrical charges from articles comprising the steps of:

(a) supplying water from a source thereof for ozonation;

(b) injecting ozone into the water for the ozonation;

(c) sensing when articles are present (d) contacting the articles, having a static electrical charge associated therewith, with the ozonated water; and (e) substantially eliminating static electrical charges from the articles by supplying ozonated water to contact the articles when the articles are present.

10. A method for substantially eliminating static electrical charges from articles comprising the steps of:

(a) supplying water from a source thereof for ozonation;

(b) injecting ozone into the water for the ozonation;

(c) returning at least a predetermined first portion of the ozonated water to the source through means arranged for bypassing the articles; and (d) supplying a predetermined second portion of the ozonated water to the articles, when the concentration of ozone in the ozonated water is sufficient, for substantially eliminating static electrical charges associated with the articles.

11. A method according to claim 10 further comprising the steps of:

(a) establishing a set point for maximum loss of ozone concentration over time;

(b) monitoring the concentration of ozone in the water being returned to the source with respect to time; and (c) ceasing to supply ozonated water when the monitored concentration of ozone in the water being returned to the source exceeds the set point for maximum ozone loss over time.

12. A method according to claim 11 wherein the step of ceasing to supply ozonated water is automatically controlled in response to the monitored concentration of ozone in the water being returned to the source.

* * * * *

UNITED STATES PATENT AND TRADEMARK OFFICE
CERTIFICATE OF CORRECTION

PATENT NO. : 5,598,316

DATED : January 28, 1997

INVENTOR(S) : Kasting, Jr.

It is certified that error appears in the above-identified patent and that said Letters Patent is hereby corrected as shown below:

```
On the cover page, U.S. Patent Documents, please insert
-- 3,302,655  02/07/67  Sasaki et al. --.

On the cover page, U.S. Patent Documents, please insert
-- 3,476,600  11/04/69  Morgan, Jr. et al. --.

On the cover page, U.S. Patent Documents, please insert
-- 3,490,467  01/20/70  Gore et al. --.

On the cover page, U.S. Patent Documents, please insert
-- 3,796,925  03/12/74  Breeding --.

On the cover page, U.S. Patent Documents, please insert
-- 3,896,827  07/29/75  Robinson --.

On the cover page, U.S. Patent Documents, please insert
-- 4,280,520  07/28/81  Fraula et al. --.

On the cover page, U.S. Patent Documents, please insert
-- 4,313,767  02/02/82  Bemis et al. --.

On the cover page, U.S. Patent Documents, please insert
-- 4,434,069  02/28/84  Fairchild --.

On the cover page, U.S. Patent Documents, please insert
-- 4,505,836  03/19/85  Fairchild --.
```

UNITED STATES PATENT AND TRADEMARK OFFICE
CERTIFICATE OF CORRECTION

PATENT NO. : 5,598,316

DATED : January 28, 1997

INVENTOR(S) : Kasting, Jr.

It is certified that error appears in the above-identified patent and that said Letters Patent is hereby corrected as shown below:

On the cover page, U.S. Patent Documents, please insert -- 4,795,497  01/03/89  McConnell et al. --.

On the cover page, U.S. Patent Documents, please insert -- 5,082,558  01/21/92  Burris --.

On the cover page, U.S. Patent Documents, please insert -- 5,106,495  04/21/92  Hughes --.

Column 2, cover page, line 3, "Kasting et al." should be -- Kasting, Jr. et al. --.

Column 5, line 3, "11" should be -- 11 --.

Column 5, line 45, after "12" insert -- . --.

Column 5, line 63, "1" should be -- 10 --.

UNITED STATES PATENT AND TRADEMARK OFFICE
CERTIFICATE OF CORRECTION

PATENT NO. : 5,598,316
DATED : January 28, 1997
INVENTOR(S) : Kasting, Jr.

It is certified that error appears in the above-indentified patent and that said Letters Patent is hereby corrected as shown below:

Column 7, line 8, "12" should be -- 102 --.

Column 10, line 67, after "present" insert -- ; --.

Signed and Sealed this

Third Day of June, 1997

BRUCE LEHMAN

Attest:

Attesting Officer

Commissioner of Patents and Trademarks